US00PP24546P3

(12) United States Plant Patent
Egger

(10) Patent No.: US PP24,546 P3
(45) Date of Patent: Jun. 10, 2014

(54) ***HEUCHERA* PLANT NAMED 'COCO'**

(50) Latin Name: ***Heuchera* hybrid**
Varietal Denomination: Coco

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 141 days.

(21) Appl. No.: 13/507,938

(22) Filed: Aug. 7, 2012

(65) Prior Publication Data

US 2014/0047604 P1 Feb. 13, 2014

(51) Int. Cl.
*A01H 5/00* (2006.01)

(52) U.S. Cl.
USPC ..... Plt./440

(58) Field of Classification Search
USPC ..... Plt./440
See application file for complete search history.

*Primary Examiner* — Susan McCormick Ewoldt
(74) *Attorney, Agent, or Firm* — Klarquist Sparkman, LLP

(57) ABSTRACT

A new and distinct *Heuchera* plant characterized by medium small glossy dark brown to black leaves, light pink buds to white flowers, repeat blooming on short, dark flower stalks, small, multi-crowned, low mounding habit, and excellent vigor.

1 Drawing Sheet

Botanical denomination: *Heuchera* hybrid.
Variety designation: 'Coco'.

BACKGROUND OF THE INVENTION

The present invention relates to a new and distinct cultivar of *Heuchera* and given the cultivar name of 'Coco'. *Heuchera* is in the family Saxifragaceae. *Heuchera* 'Coco' originated from a controlled cross between *Heuchera* K409-2, a proprietary non-commercial hybrid, as the seed parent, and *Heuchera* K367-2, a proprietary non-commercial hybrid, as, as the pollen parent.

Compared to the seed parent, *Heuchera* K409-2, the new cultivar has leaves that are almost black rather than khaki in color.

Compared to the pollen parent, *Heuchera* K367-2, the new cultivar has smaller leaves and light pink flowers rather than creamy yellow.

Compared to *Heuchera* 'Obsidian', U.S. Plant Pat. No. 14,836, the new cultivar has more crowns, leaves that are more lobed, and much shorter flowering stems.

Compared to *Heuchera* 'Blackout', U.S. Plant Pat. No. 20,613, the new cultivar has leaves that are brown to black rather than purple black to olive green, the leaves are less glossy, and the leaf lobes that are more rounded.

This new *Heuchera* is uniquely distinguished by:

1. medium small glossy dark brown to black leaves,
2. light pink buds to white flowers,
3. repeat blooming on short, dark flower stalks,
4. small, multi-crowned, low mounding habit, and
5. excellent vigor.

This new cultivar has been reproduced only by asexual propagation (tip cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWINGS

FIG. 1 shows a nine-month-old plant of *Heuchera* 'Coco' growing in a one gallon pot in a cool greenhouse in early June in Canby, Oreg.

FIG. 2 shows an 11 month old plant of the new cultivar in the late July.

DETAILED PLANT DESCRIPTION

The following is a detailed description of the new *Heuchera* cultivar based on observations of two-year-old specimens growing in one gallon containers in a warm greenhouse in April in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The *Royal Horticultural Society Colour Chart,* 2007 edition.

Plant:

*Form.*—Basal rosette, herbaceous perennial.
*Hardiness.*—USDA Zone 4 to 9.
*Size.*—17 cm tall from top of the foliage to the soil and 33 cm wide.
*Habit.*—Mounding.
*Vigor.*—Excellent.

Leaf:

*Type.*—Simple.
*Arrangement.*—Rosette.
*Number.*—About 50.
*Shape.*—Broadly ovate.
*Lobing/division.*—5 lobes with shallow secondary lobes.
*Venation.*—Palmate.
*Margins.*—Crenate, slightly wavy.
*Apex.*—Mucronulate.

*Base*.—Cordate, lobes sometimes overlapping.
*Blade size*.—Grows to 10 cm long and 10 cm wide.
*Texture*.—Supple.
*Surface texture*.—Glandular on top and bottom side.
*Petiole description*.—Grows to 17 cm long and 2 mm wide, glandular hairs, Greyed Purple 187A.
*Leaf color*.—Topside, spring to summer, Brown 200A with veins Greyed Purple 187A, bottom side closest to Red Purple 59A; fall to winter, topside closest to Black 203A with veins Greyed Purple 187A.

Inflorescence:
*Size*.—Grows to 3.5 cm wide and 11.5 cm long.
*Type*.—Thyrse.
*Number of flowers per thyrse*.—About 50.
*Number of thyrse*.—About 25 in the first spring flush, reblooming all summer to frost.
*Peduncle*.—Grows to 24 cm long, 3 mm wide at base, Purple N77A, glandular hairs.
*Pedicel*.—Variable in size, with glandular hairs, Purple N77A.
*Bloom period*.—May through October in Canby, Oreg.

Flower bud:
*Size*.—3 mm wide and 3.5 mm long.
*Description*.—Glandular puberulent, ovoid, down facing.
*Color*.—Red Purple 65B on the bottom ½ and 65D on the top ½.

Flower:
*Type*.—Perfect.
*Shape*.—Campanulate.
*Size*.—6 mm long and 4 mm wide.
*Corolla description*.—5 petals, 3.5 mm long and 0.5 mm wide, narrowly spatulate, margins entire, tip acute, glabrous top and glandular on bottom, White NN155C.
*Calyx description*.—Campanulate, 5 mm long and 4 mm wide, with 5 lobes divided ⅓ to the base, each 1.5 mm wide and 2 mm long, glandular hairs outside and inside, tips obtuse, margin entire; color outside and inside White NN155B with tints of Red Purple 65B on bottom ⅓.
*Stamen description*.—5 in number, filaments 1.5 mm long, White NN155C, anthers 0.2 mm, Orange 30A, pollen Orange 28A.
*Pistil description*.—1, 2-beaked, 6 mm long and 2.5 mm wide, NN155C overall; ovary 2.5 mm long and 2.5 mm wide, style 2.5 mm long.
*Fragrance*.—None.
*Lastingness*.—Each thyrse blooms for about 3 weeks on the plant.

Fruit:
*Type*.—Two-beaked ovoid capsule.
*Fertility*.—Low.
*Color*.—Greyed Brown 199C.
*Size*.—4 mm long and 3 mm wide.

Seed:
*Shape*.—Linear.
*Size*.—2 mm long.
*Color*.—Black 202A.

Pest and disease tolerance: The new cultivar is typical to the genus. No known resistances to pests or diseases. No problems have been found in Canby, Oreg.

I claim:

1. A new and distinct *Heuchera* plant as herein illustrated and described.

* * * * *

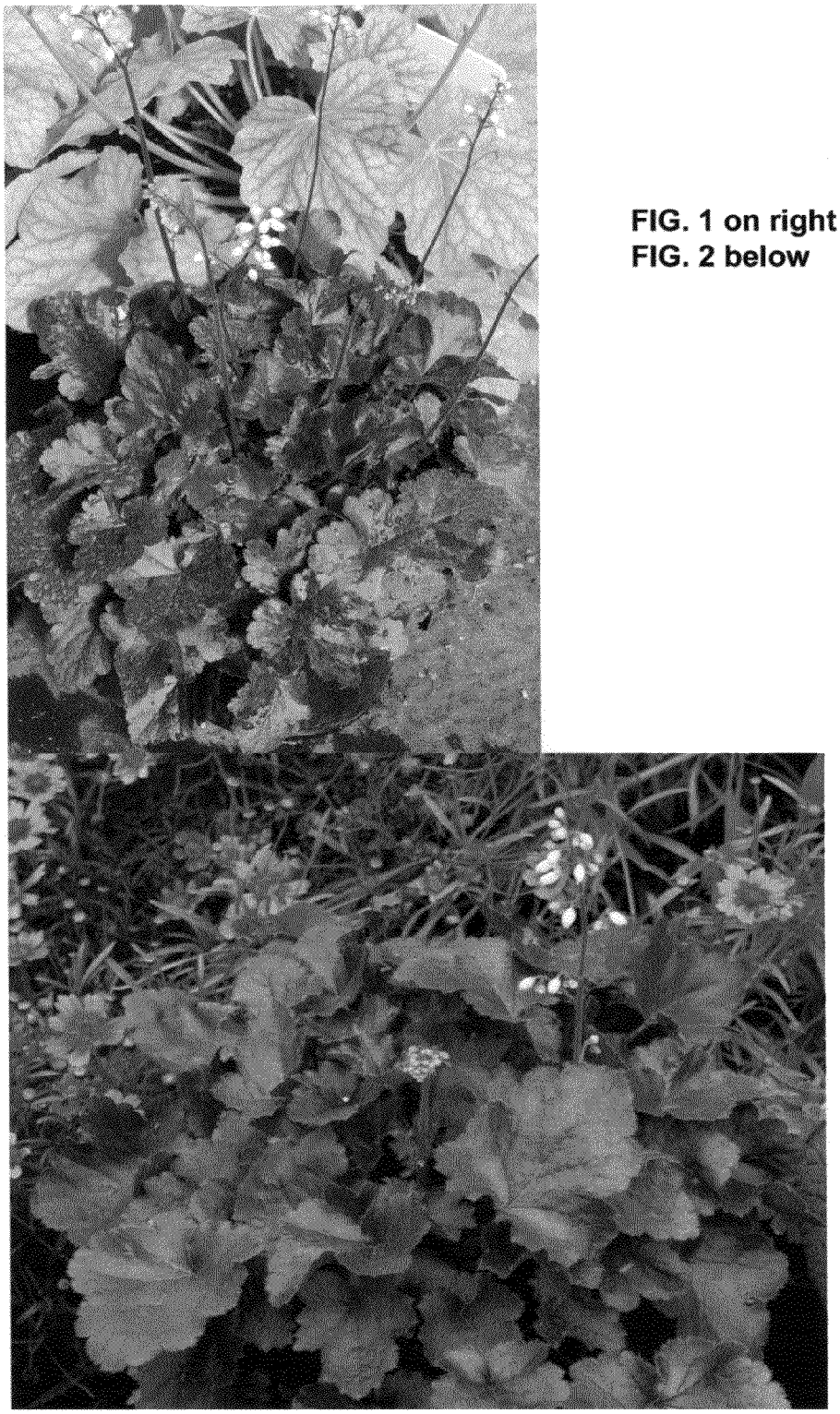
FIG. 1 on right
FIG. 2 below